United States Patent [19]

Mickols

[11] Patent Number: 5,100,802

[45] Date of Patent: Mar. 31, 1992

[54] FLUORESCENT MONITORING METHOD FOR POLYMERIZATION REACTIONS

[75] Inventor: William E. Mickols, Martinez, Calif.

[73] Assignee: The Dow Chemical Company, Midland, Mich.

[21] Appl. No.: 446,273

[22] Filed: Dec. 5, 1989

[51] Int. Cl.[5] .................... G01N 21/64; G01N 21/76; G01N 33/44

[52] U.S. Cl. ........................................ 436/34; 436/56; 436/85; 436/172; 436/903

[58] Field of Search .................... 436/34, 56, 85, 172, 436/903; 534/588, 689

[56] References Cited

U.S. PATENT DOCUMENTS

| | | | |
|---|---|---|---|
| 4,651,011 | 3/1987 | Ors et al. | 250/459.1 |
| 4,717,674 | 1/1988 | Sung | 436/85 |
| 4,810,438 | 3/1989 | Webster et al. | 264/40.6 |

OTHER PUBLICATIONS

Wang, Francis et al., "Novel Fluorescence Method for Cure Monitoring of Epoxy Resins", Polymer 1986, 27(10), 1529–32.
CA 100:122117x—Levy, R. L. et al.; *Org. Coat. Appl. Polym. Sci. Proc.* 1983, 48, 116–20.
CA 101:24337v—Levy, R. L.; *Polym. Mater. Sci. Eng.* 1984, 50, 124–9.
CA 103:38034x—Sung, Chong Sook Paik; *Macromolecules* 1985, 18(7), 1510–12.
CA 103:196714y—Wang, Francis W.; *Polym. Mater. Sci. Eng.* 1985, 53, 180–4.
CA 104:150025s—Levy, R. L.; *Polym. Mater. Sci. Eng.* 1986, 54, 321–4.
CA 104:186964m—Scarlata, Suzanne F.; *Polym. Commun.* 1986, 27(2), 41–2.
CA 105:192136e—Wang, Francis W. et al.; *Polym. Prepr. (Am. Chem. Soc., Div. Polym. Chem.)* 1986, 27(2), 306–7.
CA 105:209848p—Sung, C. S. P. et al.; *Polym. Prepr. (Am. Chem. Soc., Div. Polym. Chem.)* 1986, 27(2), 308–9.
CA 105:227482u—Sung, Chong Sook Paik et al.; *Macromolecules* 1986 19(12), 2922–32.
CA 106:214872s—Levy, R. L. et al.; *Polym. Mater. Sci. Eng.* 1987, 56, 169–74.
CA 107:97347g—Irie, Masahiro; *Kagaku (Kyoto)* 1987, 42(6), 424–5.
CA 108:113106f—Wang, F. W. et al.; *ACS Sympos. Ser.* 1987, 358 (Photophys. Polym.) 454–62.
CA 108:168508u—Stroeks, A. et al.; *Polymer* 1988, 29(3), 467–70.
CA 109:74459x—Yu, W. C. et al.; *Polym. Prepr. (Am. Chem. Soc., Div. Polym. Chem.)* 1988, 29(1), 532–3.
CA 109:94125p—Levy, R. L. et al.; *ACS Symp Ser. (Cross-Linked Polym.)*, 113–21, 1988.
CA 110:247690p—Schwab, S. D. et al.; *Polym. Mater. Sci. Eng.*, 59, 591–5, 1988.
CA 103:142797j—Levy, R. L. et al.; *Polym. Sci. Technol.* 1984, 29, 245–56.
Loutfy, Rafik O.; *Macromolecules*, 1981, 14, 270–275.
Tredwell, Colin J. et al.; *Faraday II*, 1980, 76, 1627–1637.
Dong, Dao Cong et al.; *Can. J. Chem.*, 1984, 62, 2560–2565.

*Primary Examiner*—David L. Lacey
*Assistant Examiner*—David Redding
*Attorney, Agent, or Firm*—Janet Pauline Clark

[57] ABSTRACT

Disclosed is a method for measuring the rate and extent of cure of a resin system undergoing polymerization which entails adding at least one multifunctional fluorescent dye to the resin system undergoing polymerization, the dye being one which initially forms a complex with itself or other components of the system and subsequently chemically reacts with the resin and whose degree of fluorescent emission varies in accordance with the degree of reaction with the resin, polymerizing the resin, simultaneously measuring the fluorescence of the resin system, and comparing the measured fluorescence with pre-existing data correlating the observed values with the rate and extent of polymerization, thereby enabling the rate and extent of polymerization of the resin system under evaluation to be determined.

18 Claims, 9 Drawing Sheets

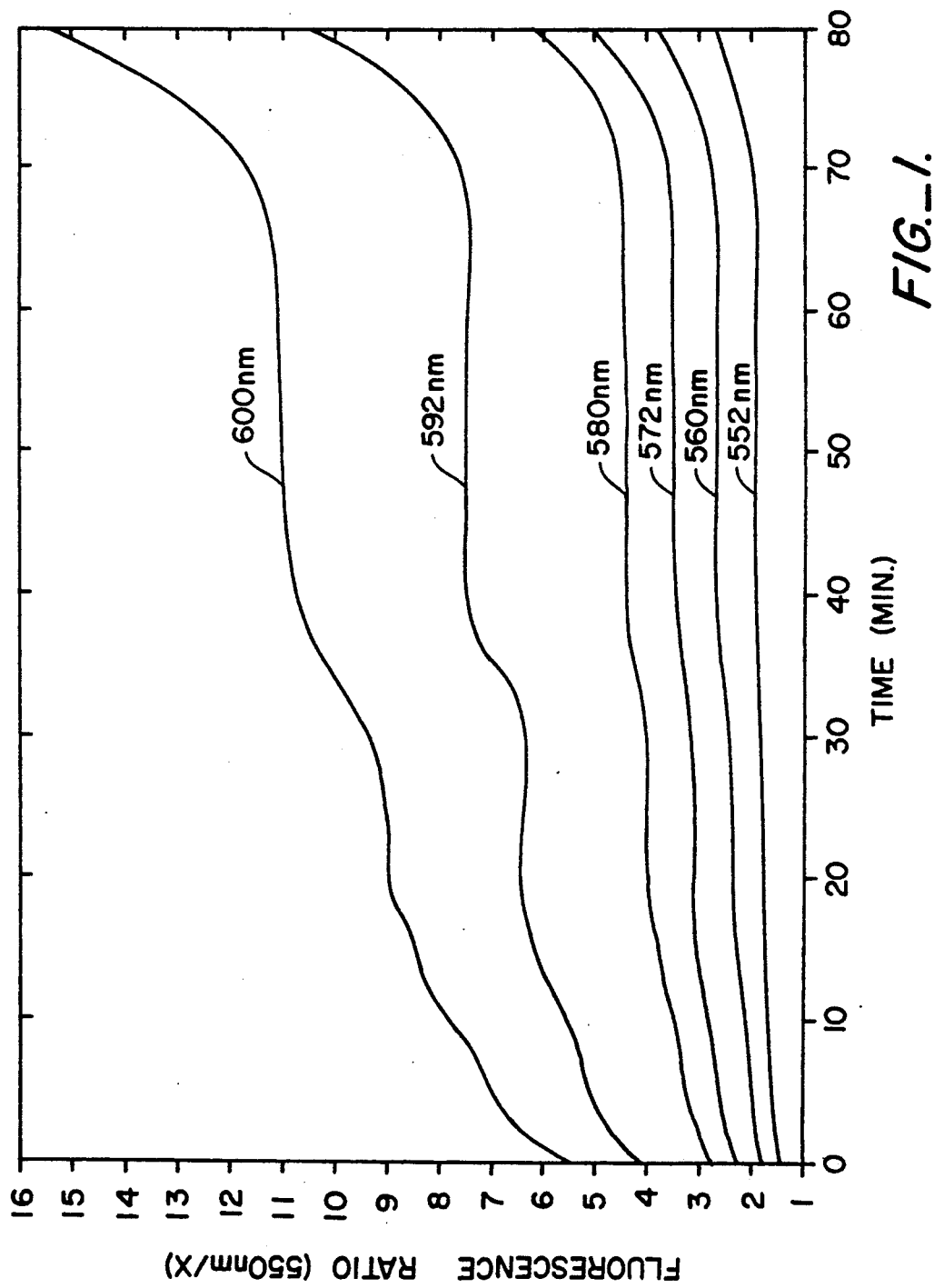

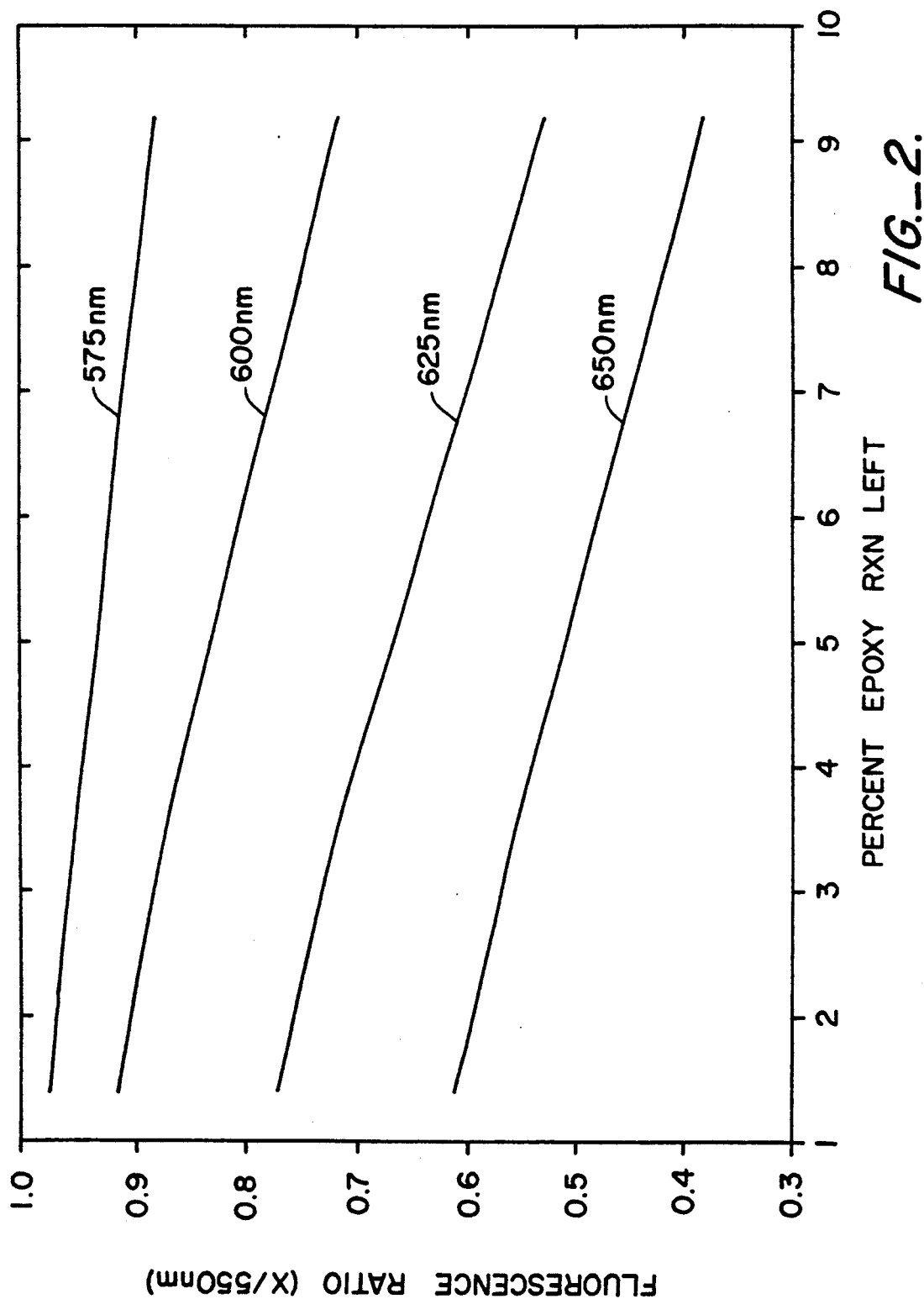
FIG._2.

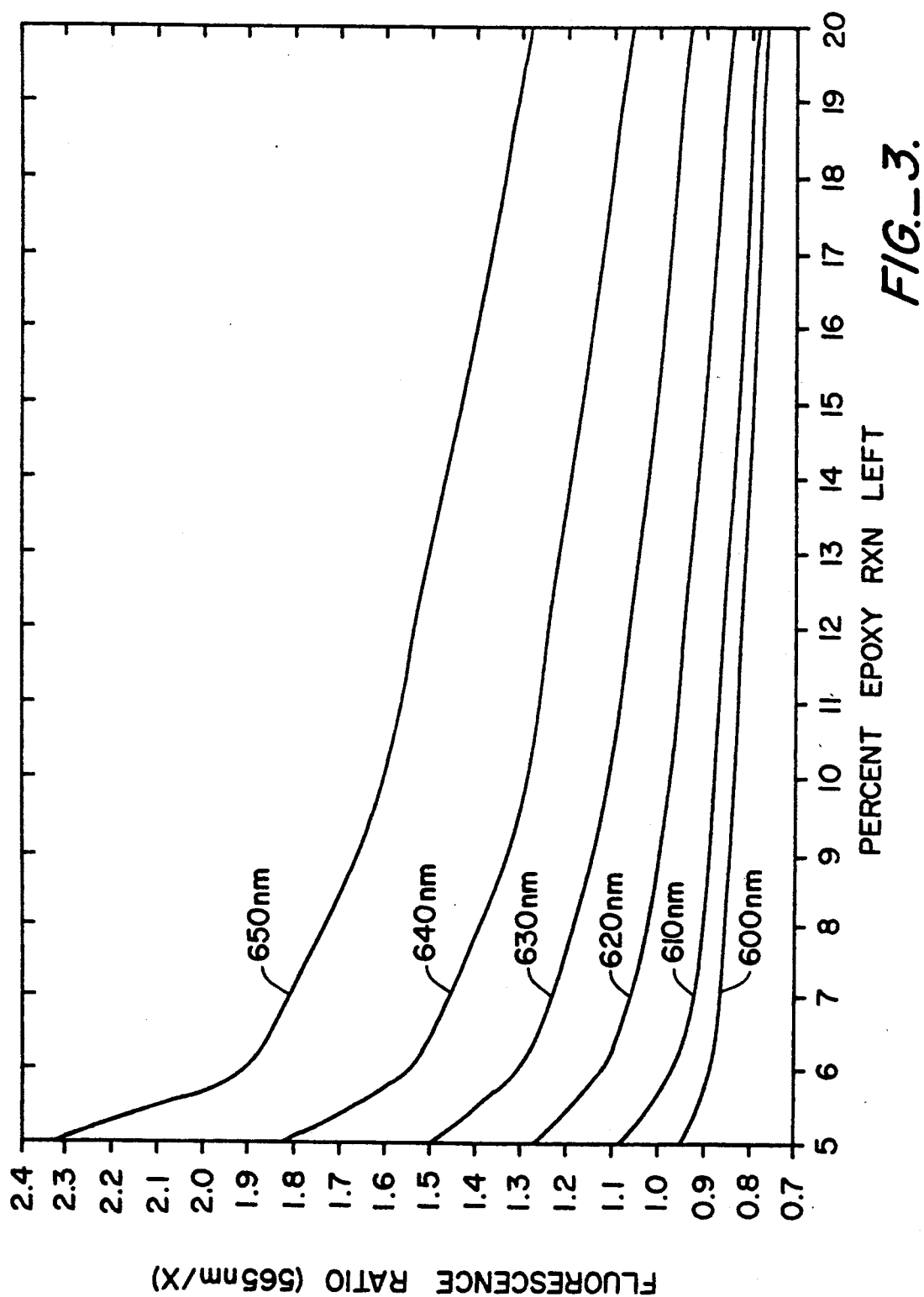
FIG._3.

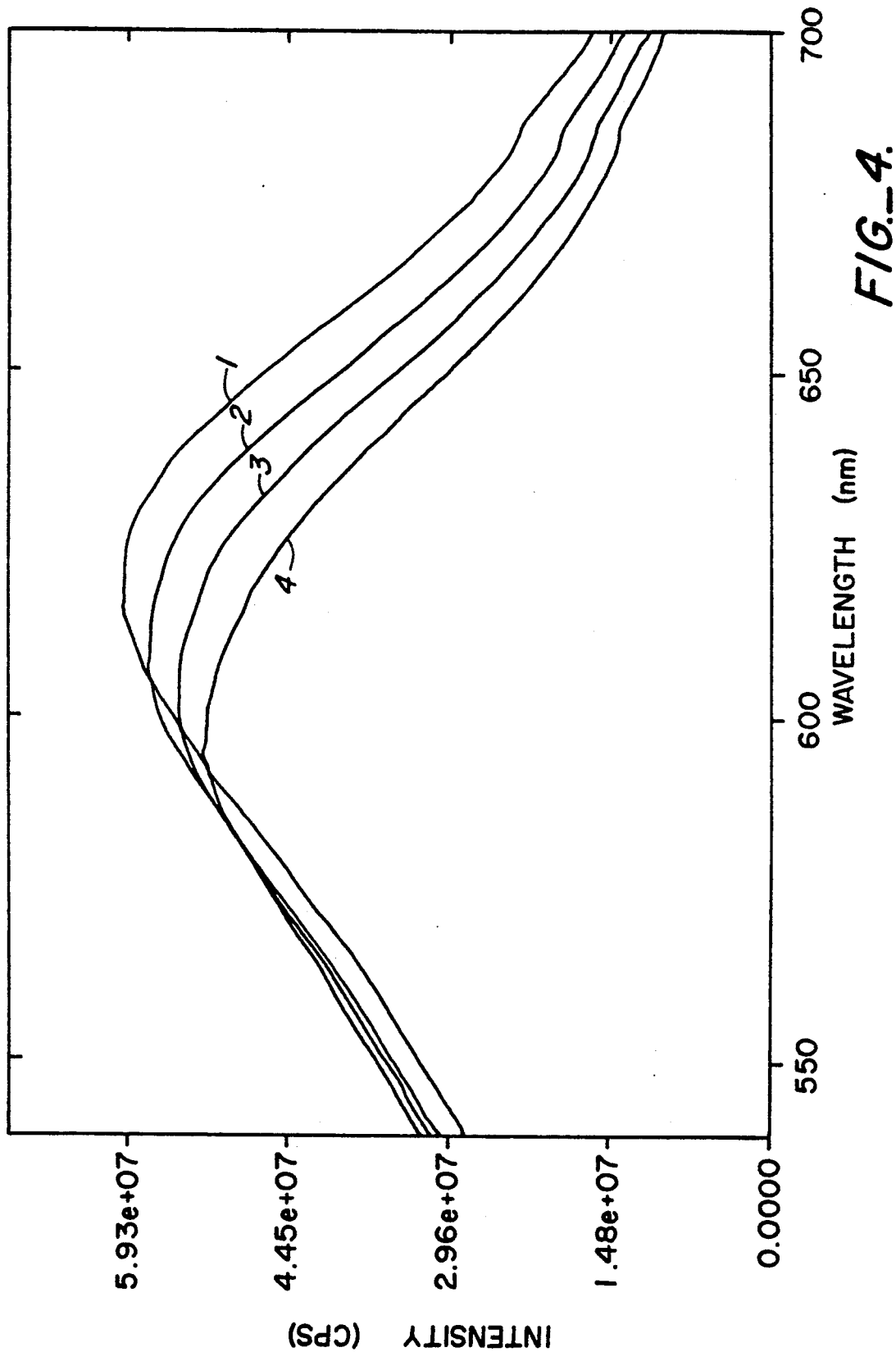
FIG._4.

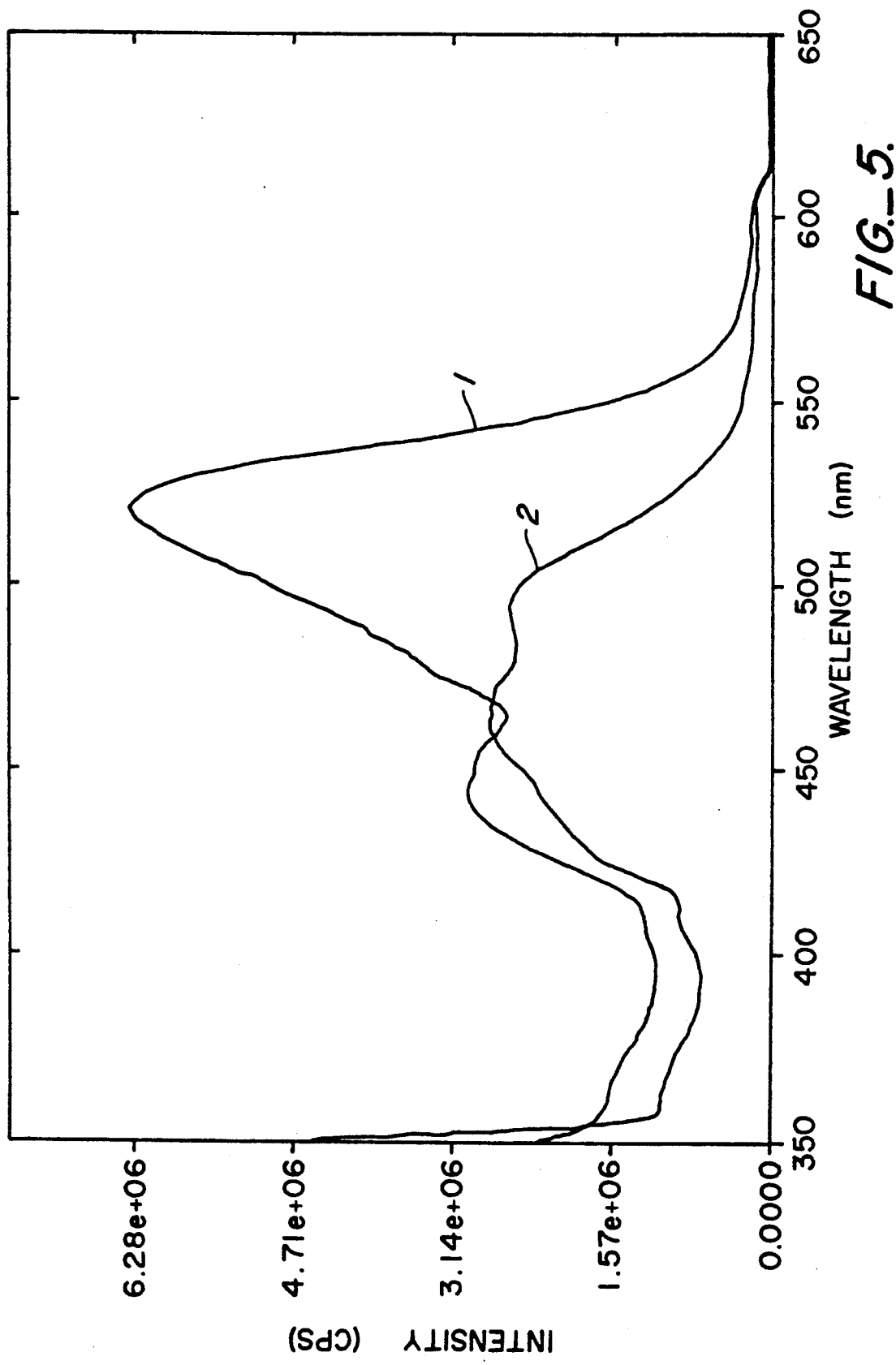
FIG._5.

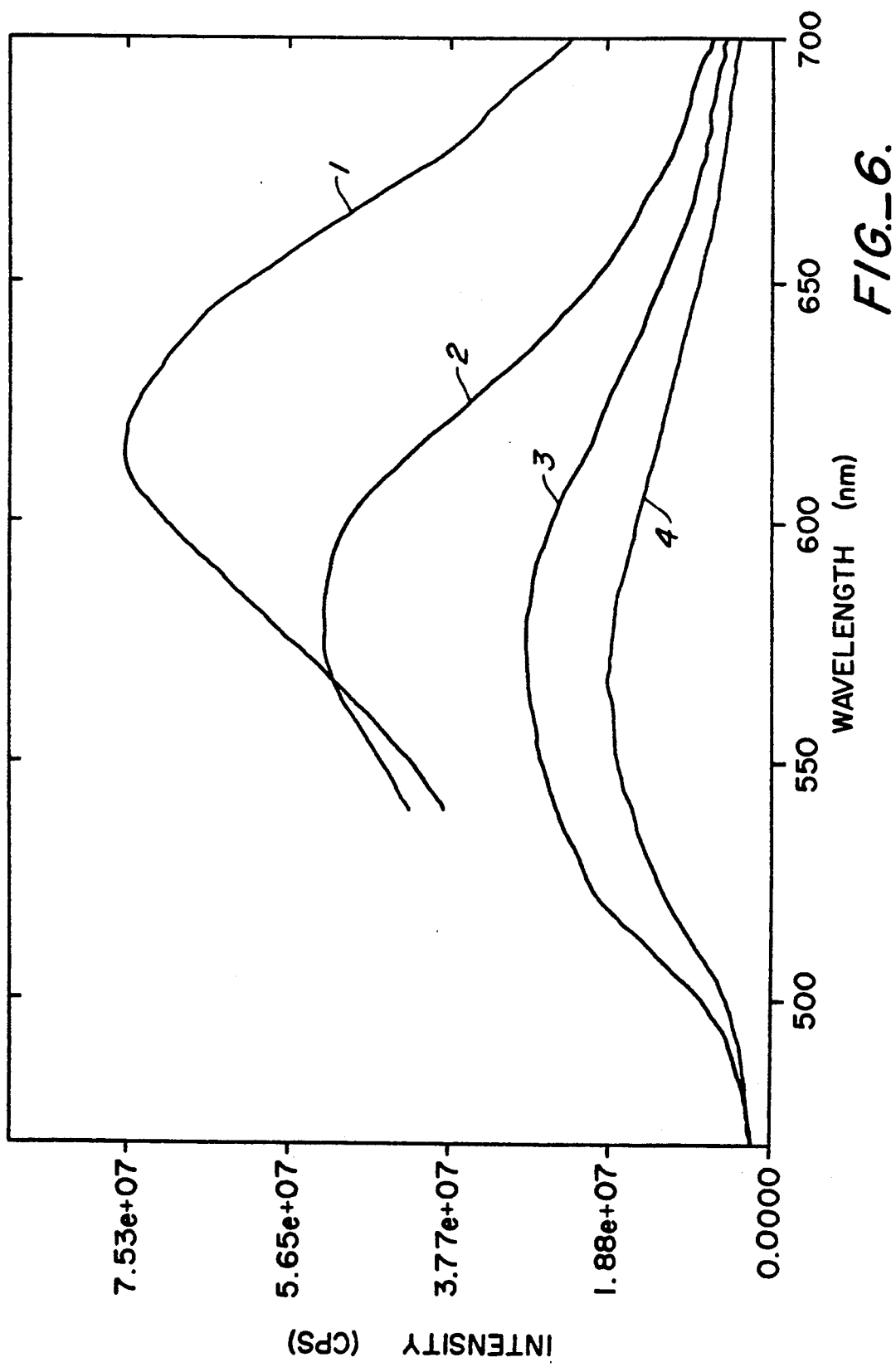

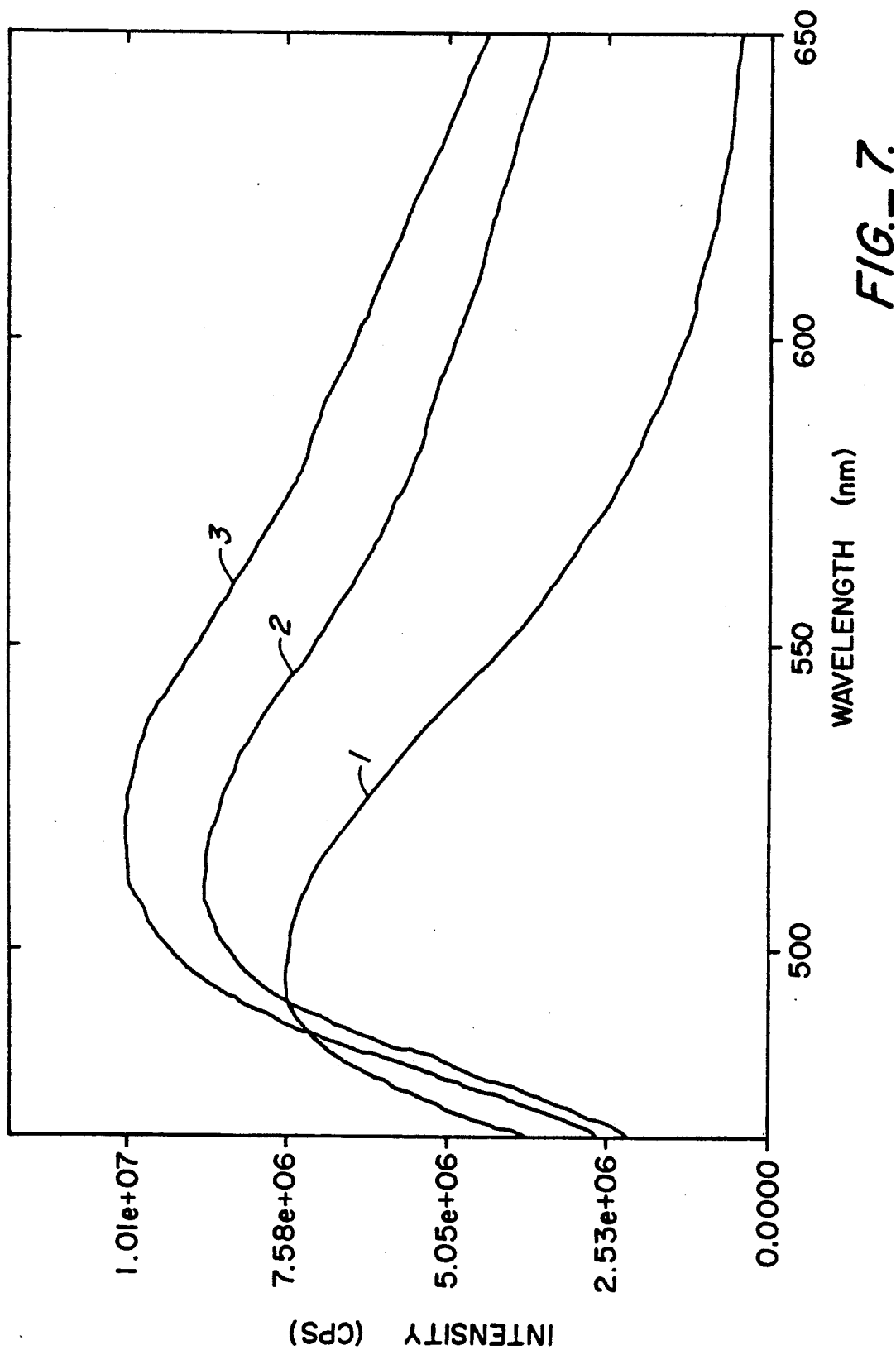
FIG._7.

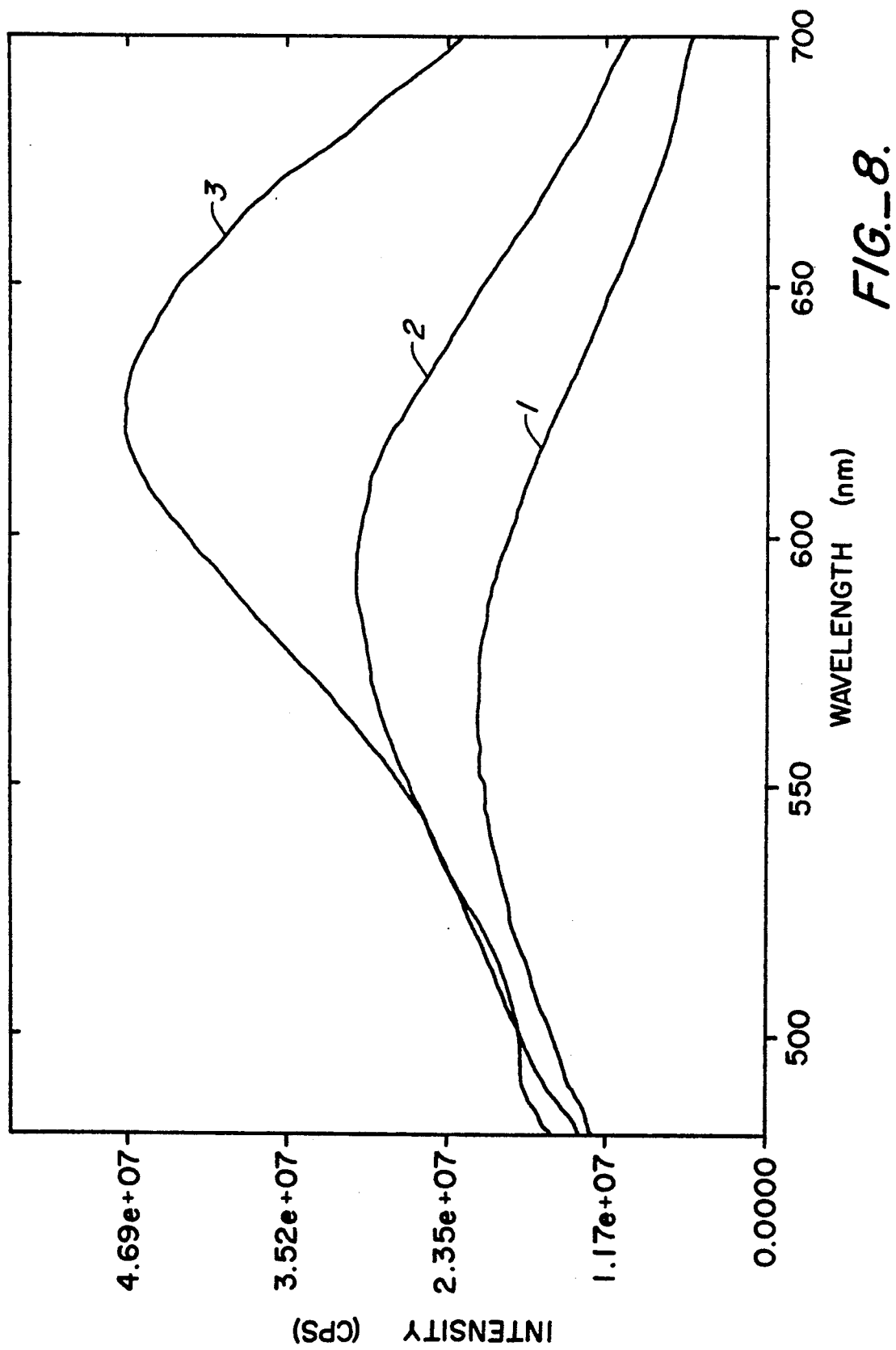

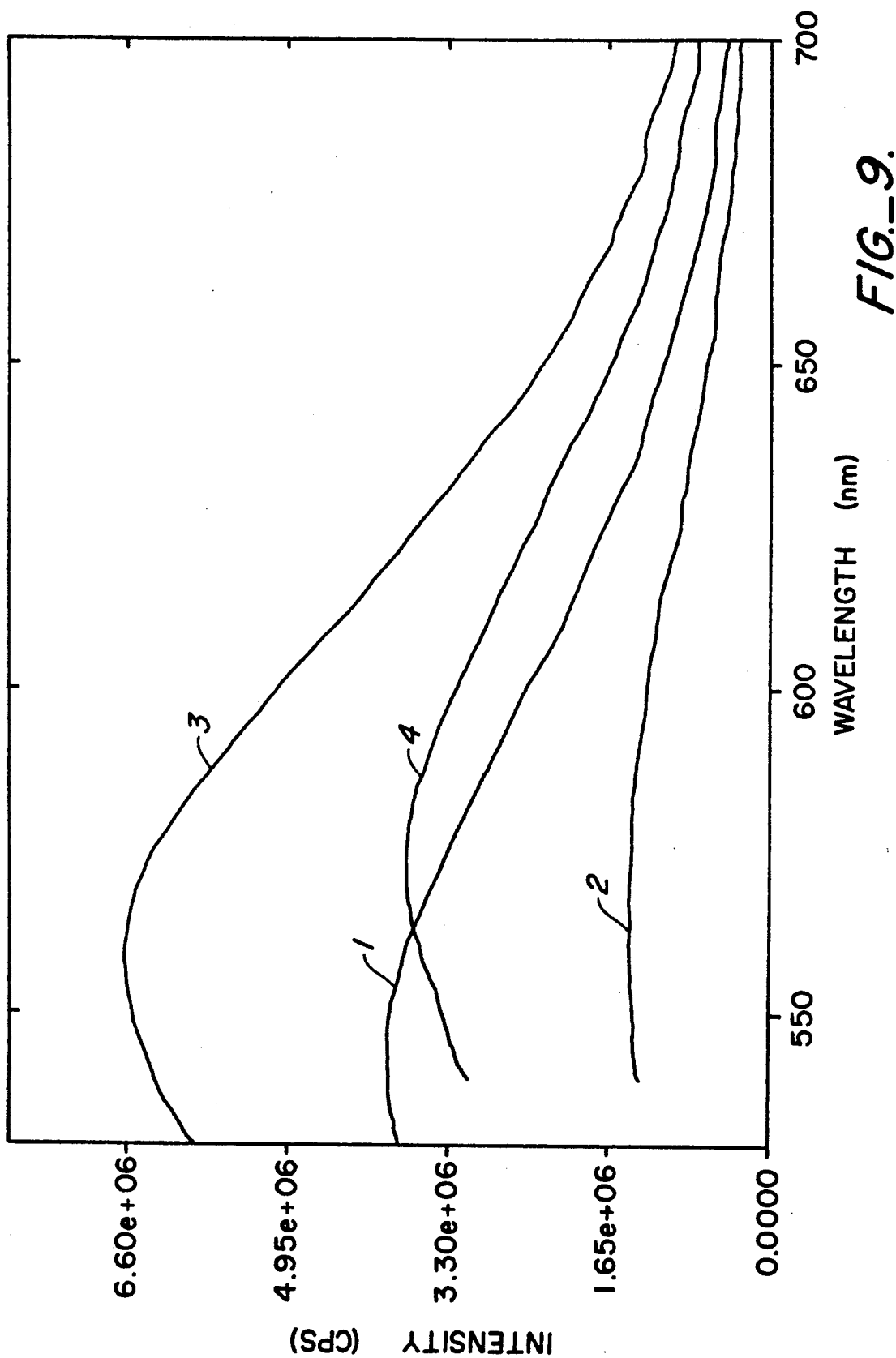
FIG._9.

FLUORESCENT MONITORING METHOD FOR POLYMERIZATION REACTIONS

BACKGROUND OF THE INVENTION

This invention relates to a method for measuring the physical-chemical kinetics of resin systems undergoing polymerization. Specifically, it relates to a method for monitoring the extent and determining the rate of cure of resin systems undergoing polymerization by incorporating into the resin system a fluorescent dye which reacts with the resin and changes the fluorescence in proportion to the extent of cure of the resin.

Polymerized resin systems are widely used in this and foreign countries for a variety of purposes. In general, any plastic structure, whether thermoplastic or thermosetting, is derived from a polymerized resin system.

Epoxy resins, for example, are commercially used in coating and structural applications. They are frequently used as fiber-reinforcing materials in the production of laminates and composites. Printed wiring boards used in electronic devices, in particular, are made from epoxy resin-based laminates or composites. Epoxies are used because of their hardness, resistance to corrosive environments, and relatively low dielectric constants.

The quality and properties of composite parts made from epoxy resins depend on several factors, including the proper cure of the epoxy resin. Variations in time and temperature, and polymer composition all affect the proper curing. Typically, the composites are cured for excessive lengths of time to insure the complete cure of the epoxy resin. The ability to monitor the epoxy curing process on line for the fabrication of composite parts would provide several advantages over existing methods. Correct cure cycles could be identified to prevent incomplete cure of the epoxy resin. Incomplete cure results in a loss of strength of the composite, a lack of uniformity in the physical characteristics, and undesirable variations in the dielectric constant. It also affects the thermal stability of the end product. The ability to identify correct cure cycles is especially important in the production of high-cost parts, where increasing the production rate while maintaining quality would be valuable In addition, part quality could be inspected by randomly sampling the extent of epoxy cure. Finally, the cure could be monitored in different regions of large or complex parts to insure homogeneous properties in the final product.

Epoxy resins are characterized by a 3-membered ring known as the epoxy, epoxide, oxirane, or ethoxylene group. These resins are prepared by the reaction of compounds containing an active hydrogen group with epichlorohydrin, followed by dehydrohalogenation. Optimum performance properties are obtained by cross-linking the epoxy resins into a three-dimensional insoluble and infusible network To accomplish this, the resin is treated with a curing agent or hardener The specific choice of curing agent or hardener depends on processing methods, curing conditions, and the specific physical and chemical properties desired. Primary and secondary amines are the most widely used curing agents for epoxy resins.

The structure and properties of epoxies are known to strongly depend on the extent of cure and physical aging which has taken place after the cure cycle is completed. The curing of a thermoset epoxy resin can be expressed in terms of a time-temperature-transformation relationship. There are normally considered to be four distinct states of the thermosetting-curing process: liquid, gelled rubber, ungelled glass, and gelled glass. The time-temperature-transformation diagrams can be used to establish chemical structure-physical property relationships of fully cured systems, since each system is unique in the kinetic before final cure and the physical properties it imparts. The extent of cross-linking is a measure of the degree of cure. The most favorable properties, i.e., high strength, thermal stability, chemical resistance, etc., are obtained by maximum cross-linking.

THE PRIOR ART

A number of physical chemical techniques have been used or developed to measure the degree of cure and physical aging in epoxies and other polymer systems. The two most widely used techniques to monitor epoxy cure at the present time follow first, sample temperature and second, dielectric properties during the cure process. However, there are disadvantages to using these techniques. The use of thermocouples to monitor the temperatures provides insufficient information of the cure. This is due to complicated heat transfer mechanisms of the system. Complex diconvolution routines are required to separate heat transfer phenomenon from actual sample temperature effects. Dielectrometry, although applicable for some processes, is limited because the sensors are too large to be included in a part. Furthermore, the sensors are expensive and are not feasible in use in high-volume applications. Other monitoring systems have been developed, although none are in commercial use at the present time.

U.S. Pat. No. 4,810,438, discloses a technique for controlling the curing process of fiber-reinforced composite materials that are formed using thermosetting resins. The technique is described as a percent gel method which involves development of a time-to-gel equation as a function of temperature. From this equation, a rate-of-gel equation is then determined, and a percent gel is calculated which is the product of rate-of-gel times time. The percent gel accounting is used to control the proper pressure application point in an autoclave cure process to achieve desired properties in a production composite part.

Levy et al., in an article in *Polym. Sci. Technol.* Plenum) 1984, 29, (Adhes. Chem.), pp. 245-56, describes the utilization of a viscosity-dependent fluorescence probe for in-situ monitoring of epoxy cure kinetics. In this method, the fluorescence emission spectrum of a probe-containing specimen is recorded at room temperature after each curing interval at the selected cure temperature. A parallel series of spectra is reported of an epoxy specimen which does not contain the fluorescence probe. The reference series of fluorescence emission spectra is recorded to ascertain that the observed increase of fluorescence results solely from increase of the fluorescence quantum yield of the probe. The fluorescence measurements are performed using a fluorometer. The fluorescence probe used is "polyester yellow" dye, one of a series of p-(N,N-dialkylamino)benzylidene malononitriles.

Another article by the same author in *Polym. Mater. Sci. Eng.* 1987, 56, pp. 169-74 describes a cure sensor which is based on the combination of fiber optic fluorometry and viscosity-degree of cure dependence of the resin fluorescence. The resin fluorescence observed in this system is not due to a fluorescent probe, but rather to alleged impurities in the resin.

Yet another article by the same author appearing in *Polym. Mater. Sci. Eng.* 1984, 50, pp. 124–9 describes the self-probe fluorescence of an epoxy resin in which the intensity of the fluorescence as a function of cure time was continuously recorded. In this article it is stated that viscosity-dependent fluorescence rises when excited molecules can undergo internal conversion (deactivation) via intermolecular torsional or twisting motions thus leading to low fluorescence quantum yields. It is further stated that when the viscosity of the medium gradually increases, as it does in polymerization reactions, such torsional relaxation becomes progressively more inhibited leading to a gradual increase of the fluorescence quantum yield. The conclusion is thus drawn that the observed fluorescence is a function of physical characteristics.

In a further article, *Polym. Sci. Technol.* (Plenum) 1984, 29, pp. 25–86, fluorescence-derived profiles for cure kinetics which are as viscosity-dependent are described.

U.S. Pat. No. 4,717,674 discloses a method of chemical analysis and characterization of the curing of an epoxy wherein a label (azonaphthalene dye, benzylidene-dianiline dye, and conjugated stilbene dyes) is added to an epoxy system, the system then polymerized, and the fluorescence of the polymerizing system measured and compared with a curve relating fluorescent intensity to the extent of polymerization. It is stated that these dyes exhibit very sensitive changes in fluorescence intensity corresponding to emission by the label as a function of cure extent. These dyes are operative in the ultra violet spectrum.

One of the deficiencies of the prior art methods of measuring the cure rate of kinetics of epoxy systems and other resin systems is that it does not enable precise measurements to be obtained during the latter stages of the curing process.

It is particularly advantageous to be able to precisely measure the extent of cure during the latter stages of the curing process, because the processing time can be substantially reduced if the time at which curing is complete can be accurately measured. Thus, additional time does not have to be spent above and beyond the actual time required in order to insure complete cure of the resin. Additionally, since the physical properties are effected by an incompletely cured resin system, it is important to determine when the system is completely cured in order to avoid the production of substandard products.

It would be desirable in the art, therefore, to develop a method for the measurement of cure rate kinetics of epoxy and other systems which is highly sensitive with respect to the latter stages of the curing reaction By the term "latter stages" is meant preferably about the last 50 percent of the cure reaction, more preferably about the last 25 percent of the cure reaction, even more preferably about the last 10 percent of the cure reaction, as measured by the amount of energy given off during the cure.

This invention is concerned with such a method.

It is therefore an object of the present invention to provide a method for determining the extent and rate of cure in epoxies and other resin systems such as urethanes during the curing reaction.

It is another object of the present invention to provide a method for determining the relative concentrations of the components or primary reaction products produced during the curing of epoxies or other thermoplastic and thermosetting resin systems.

It is yet other object of the present invention to provide a sensitive method for determining the extent and rate of cure of epoxy and other resin systems during the latter stages of the curing reaction.

SUMMARY OF THE INVENTION

The present invention is a method for measuring the rate and extent of cure of resin systems undergoing polymerization and cure. The method comprises the steps of:

A. adding a multifunctional fluorescent dye to a resin system undergoing polymerization and cure, the dye being one that during the initial stages of the cure complexes with itself or with other components of the system and chemically reacts with the resin and whose degree of fluorescence varies in accordance with the degree of chemical reaction with the resin, in an amount sufficient to produce a measurable change in fluorescence;

B. polymerizing and curing the resin;

C simultaneously measuring the fluorescence of the resin system: and

D. comparing the measured fluorescence at one or more wavelengths with pre-existing baseline values which are correlated with the extent of cure, whereby the rate and extent of cure of the system being evaluated is determined; and optionally, E. comparing the measured fluorescent emissions at one or more wavelengths with pre-existing values which are correlated with the extent of cure, whereby the rate and extent of cure of the system being evaluated is determined.

By judicious selection of the dyes which initially complex with themselves or other system components and subsequently chemically react with the resin, accurate measurements of the kinetics of epoxy or other resin system curing can be obtained, particularly with respect to the latter stages of the curing reaction.

As used herein, the term "dye" applies to an organic substance that exhibits strong adsorption of light in the visible or ultraviolet region of the spectrum without regard to any affinity for textile fibers, paper, or other substrates.

As used herein, the term "complex" as relates to the dye, refers to an intermolecular interaction between dye molecules or other components of the resin system that results in a closer average molecular distance between the dye molecules and other components of the system than would normally be expected.

A fluorescent substance is one that absorbs radiant energy of certain wave lengths and, after a fleeting instance, gives off part of the absorbed energy as quanta of longer wave lengths. In contrast to ordinary light in which the absorbed energy degrades entirely to heat, light emitted from a fluorescent dye adds color to the light returned by simple reflection.

The reaction kinetics of a resin system containing a fluorescent dye can be measured in one of two ways. A fluorescent dye both absorbs energy from light at a given wavelength and emits fluorescence at a different wavelength. It is therefore possible to determine the reaction kinetics of a system containing a fluorescent dye by either measuring the amount of "excitation", i.e., the amount of energy absorbed by the dye, or measuring the amount of emission of fluorescent light given off by the dye. The use of the term "fluorescence" or derivatives herein is intended to mean either the amount of energy absorbed by the dye, or the amount of energy given off by the dye. Both measurements can be made with the use of a standard fluorometer.

BRIEF DESCRIPTION OF THE DRAWINGS

FIG. 1 is a graph showing a number of fluorescent emission ratios calculated at different wavelengths for a fluorescent dye in an epoxy resin system.

FIG. 2 is a graph showing a comparison of the utility of different wavelengths to normalize the emission spectra of fluorescein in an epoxy resin system at different stages of cure.

FIG. 3 is a graph showing a comparison of the utility of different wavelengths to normalize the emission spectra of fluorescein in an alternate epoxy resin system at different stages of cure.

FIGS. 4 through 9 are graphs of spectral data obtained by using the method of this invention to ascertain the rate and extent of cure of various resin systems.

DETAILED DESCRIPTION OF THE INVENTION

It has now been found that when certain naturally fluorescent dyes are incorporated into polymerizing epoxy or other resin systems, the fluorescence, i.e., the amount of energy absorbed or fluorescent emissions given off, varies in proportion to the extent of the chemical reaction of the dye with the resin. This in turn is directly proportional to the extent of cure of the resin system, and thus the rate of cure of the resin system which is determined from the extent of cure. The change in energy absorbed or fluorescent emissions given off can be measured by means such as a fiber optic probe or conventional fluorometer.

Measurement of energy absorbed and/or fluorescent emissions can be accomplished by any one of four techniques. That is, the amount of light emitted or absorbed by the resin system can be measured, or the distribution of light emitted or absorbed by the system can be measured.

In a preferred embodiment of the method of the invention, a multifunctional fluorescent dye is added to the resin system undergoing polymerization and cure. The dye is one which initially complexes with itself or with other components of the system, and subsequently chemically reacts with the resin, and whose degree or amount of fluorescence varies in accordance with the degree of reaction with the resin. After the dye is added, polymerization of the resin is allowed to proceed, and simultaneously, the fluorescence or ratios of fluorescence of the resin system is measured and compared with a pre-existing curve relating fluorescence or a ratio of fluorescence intensity to the extent of polymerization.

The dyes which are used in the method of the invention are unique in that they are multifunctional. The dyes form complexes through ionic bonding and/or charge transfer with themselves or with other compounds during the early stages of the resin cure process, and during the latter stages, chemically combine with the resin to give off high intensity fluorescent emissions, thereby enabling the reaction kinetics during the latter stages of the cure process to be determined with extreme accuracy.

By the term "multifunctional" used herein, it is meant dyes which have more than one reactive site and/or dyes which have at least one reactive site capable of undergoing more than one reaction.

The terms "polymerization" and "cure" as used herein are used interchangeably, inasmuch as part of the curing process is the polymerization of the resins, i.e., linear extension, cross-linking, and the like.

The fluorescent dyes which are suitable for use of the method of this invention include (a) fluorescein and derivatives thereof, (b) acridine and derivatives thereof, and (c) polycyclic aromatics.

A preferred dye for use in the method of the invention with epoxy resins is fluorescein A. This dye is a member of the group of xanthene dyes containing the xanthylium or dibenzo-gamma-pyran nucleus as the chromophore with the amino or hydroxy groups meta to the oxygen as the usual auxochrome. Fluorescein itself has the following structure:

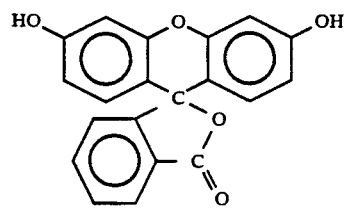

As can be seen, fluorescein possesses three reactive groups, i.e., two —OH groups, and one —$CO_2$ group. These groups are capable of forming complexes with other fluoresceins, or other epoxy resin components, by breaking the epoxide bond and attaching at that point.

In carrying out the process of this invention, it is believed that the following mechanism occurs. Initially, the fluorescein dye acts like a catalyst for the epoxy cure reaction, i.e., it forms a complex which promotes the reaction but does not enter in to it. As the reaction proceeds, however, the dye gets taken up by and is bonded to the epoxy resin.

Evidence that an initial complex of the dye is being formed, either with itself, or with other components of the resin system such as a commonly used amine curing agent, is seen in a change in emission or so called red shift in fluorescent emissions. That is, spectra of the fluorescent emissions from the dye, when incorporated into the resin system, are shifted by as much as about 50 nanometers as compared to standard spectra for the dye when it is dissolved at low concentrations in good solvents such as methanol or ethanol.

The carboxyl as well as the phenol moieties of fluorescein are known are as accelerators of the amine curing agent-epoxy reaction. These enter into the epoxy reaction but are regenerated at the end of the reaction, seldom actually reacting themselves. Only when the primary amine is decreased in concentration and the phenols are increased in concentration (due to the epoxy reaction generating phenol) does the fluorescein begin to chemically react with the epoxy. All of these phenomena combine to give a high sensitivity in the monitoring of the epoxy cure particularly during the latter stages thereof.

In addition to fluorescein, derivatives thereof can be used in the method of this invention. These derivatives include fluorescein diacetate, Rose Bengal (dibromodinitrofluorescein), Eosin B (tetraiodotetrachlorofluorescein), Eosin Y (tetrabromofluorescein), 4',5'-di-bromofluorescein, 2',7'-dichlorofluorescein, and 4',5-diiodofluorescein. Other similar derivatives can also be used.

The fluoresceins are found in several pH dependent forms, and the use of the term fluorescein or its derivatives, as used herein, is intended to cover these various forms.

The various pH dependent forms of fluorescein are shown below.

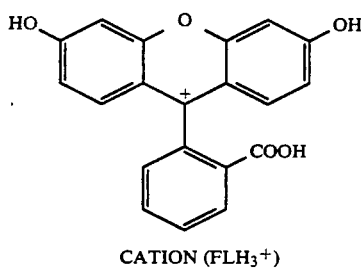

CATION (FLH$_3^+$)

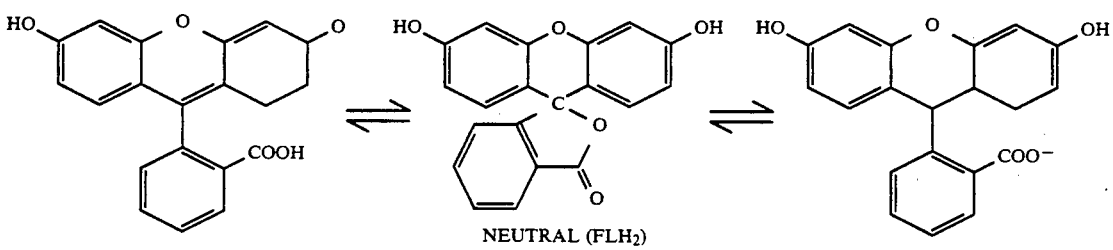

NEUTRAL (FLH$_2$)

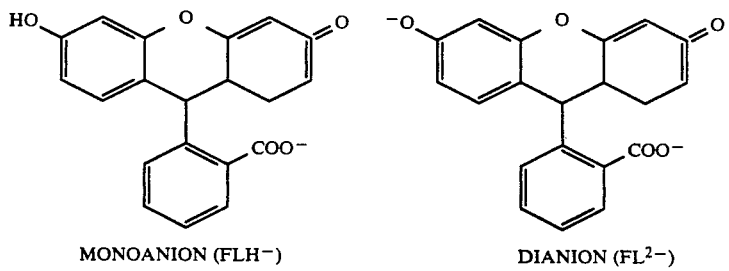

MONOANION (FLH$^-$)       DIANION (FL$^{2-}$)

Certain groups of atoms in an organic compound cause characteristic absorptions of radiation irrespective of the nature of the rest of the compound. Such groups are called chromophores or color carriers. The chromophore of fluorescein possesses the following structure:

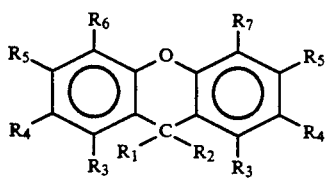

wherein $R_1$ is a carbonyl substituted phenyl group, $R_2$ is hydrogen or together with $R_1$ forms a lactone, and $R_3$, $R_4$, $R_5$, $R_6$, and $R_7$ are the same or different and are selected from the group consisting essentially of primary, secondary, or tertiary amino groups, halogen, nitro, or hydroxyl.

The acridine dyes, the second of the three categories of dyes which can be used in the method of the invention possess the structure:

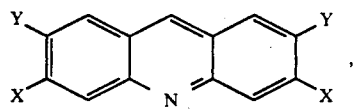

wherein X and Y are the same or different and are selected from the group consisting of hydrogen, amino, and lower alkyl.

Preferred acridine dyes for use in this invention are acridine and acridine yellow.

Acridine yellow has the structure set forth above wherein X is amino and Y is methyl.

The third class of dyes suitable for use in the method of the invention are the polycyclic aromatics.

Polycyclic aromatics are compounds characterized by repeating conjugated phenyl groups which may or may not be substituted. Preferred polycyclic aromatics for use in the process of the invention include one- and two-amino anthracene, fluoroanthene, and three-amino fluoroanthene.

The dyes are incorporated into the resin system in amounts sufficient to produce a measurable degree of the fluorescence which is required for carrying out the process. Such levels, by weight, preferably range from about 1 to about 100,000 parts per million, more preferably from about 5 to about 100 parts per million, and even more preferably from about 10 to about 40 parts per million. Fluorescein, a preferred dye used in the method of the invention with epoxy resins, is most preferably incorporated into the epoxy resin at levels ranging from about 10 to about 30 parts per million by weight relative to the epoxy resin.

The dyes which are used in the process of the invention can be incorporated into the resin system either directly into the resin itself, or the dyes may first be mixed with a curing agent or hardener and then incorporated into the resin system when the curing agent is mixed therewith. Preferably, the dye is incorporated into the curing agent, and then into the resin system when the curing agent is added to initiate the curing reaction.

Preferred epoxy resins for use in the invention include polyglycidyl ethers, esters, and amines. Preferred epoxy resins include those represented by Formulas 1-5 set forth below.

Z is a hydrocarbyl group containing from 1 to about 15 carbon atoms or a $-C(R^6)_2-C(R^6)_2-[O-C(R^6)_2-C(R^6)_2]-_{m'}$ group; A' is a divalent hydrocarbon group having from 1 to about 3, preferably 1, carbon atoms or a

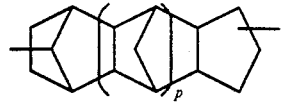

group; p has a value from zero to about 10, preferably

Formula 1

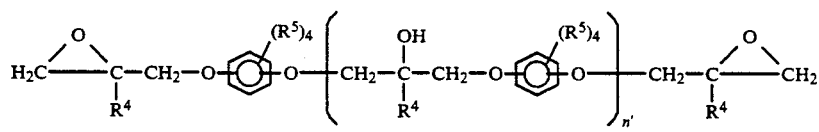

Formula 2

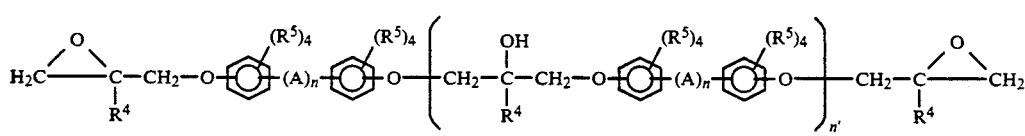

Formula 3

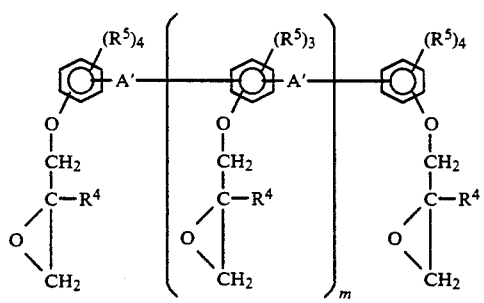

Formula 4

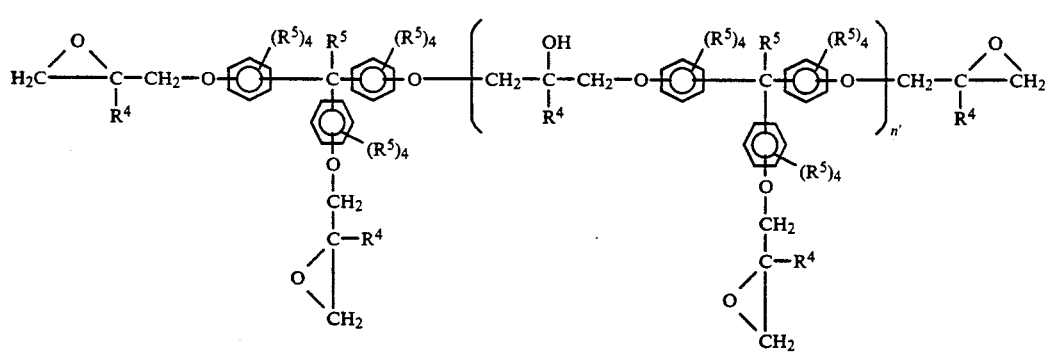

Formula 5

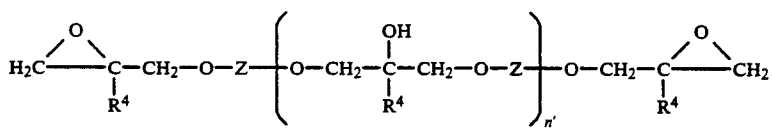

wherein A is a divalent hydrocarbon group having from 1 to about 12, preferably from 1 to about 6, more preferably from 1 to about 3, carbon atoms, $-C(CF_3)_2-$,

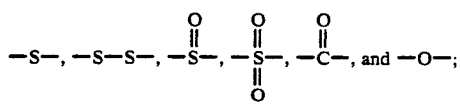

from zero to 3; each $R^4$ is independently hydrogen, a hydrocarbyl or hydrocarbyloxy group having from 1 to 18 carbon atoms or a halogen, preferably chlorine or bromine; $R^5$ is independently hydrogen or a hydrocarbyl group having from 1 to about 3 carbon atoms; each $R^6$ is independently hydrogen or a hydrocarbyl group having from 1 to about 6 carbon atoms; n has a value from zero or 1; n' has a value from zero to about 40, preferably from 0.1 to about 5; m' has a value from 1 to about 100, preferably from 1 to about 25 and m has a value from about 0.001 to about 6. Such preferred epoxy resins are more fully described in U.S. Pat. No. 4,782,124, the relevant portions of which are incorporated herein by reference for all purposes which may be legally served thereby. The epoxy resins useful in this invention preferably do not contain hydroxyl groups in amounts which cause intolerably deleterious effects in the physical properties of the cured epoxy products. Epoxy resins containing significant amounts of hydroxyl groups may be used in this invention by first reacting/blocking such hydroxyl groups in the epoxy resins. For example, the hydroxyl groups in such epoxy resins may be reacted with carbonates, preferably of low molecular weight, via a transesterification reaction as described in U.S. Pat. Nos. 4,766,184 and 4,782,124, the relevant portions of which are incorporated herein by reference for all purposes which may be legally served thereby. Preferred epoxy resins for use in the method of the invention include those sold under the designations D.E.R. ® and TACTIX ® epoxy resins, available from The Dow Chemical Company.

While the process of this invention is most advantageously used in connection with epoxy resin systems, any other thermosetting or thermoplastic resin system can be used in which the dye initially complexes with itself, or other components of the resin system, and subsequently chemically reacts with the resin in the system during the curing process.

Other resin systems would include those containing polymers such as polyethylenes, and copolymers thereof, vinyls, polystyrene and copolymers, phenolics, polypropylene and copolymers, ureas and melamines, alkyds, polyesters, acrylics, polyurethanes, polyacetals, polycarbonates, styrene-butadiene elastomers, acrylonitrile-butadiene elastomers, acrylics, and the like.

These and other resins are disclosed in *Modern Plastics Technology*, William B. Seymour, Reston Publishing Co., Inc. Reston, Va., 1975, its contents incorporated herein by reference to the extent allowed by law.

Once the dye is incorporated into the resin system, polymerization is allowed to proceed. Polymerization is accomplished by means of a curing agent or hardener, the most commonly used being an aliphatic amine in the case of epoxy resins. Suitable aliphatic amine curing agents include diethylene triamine, triethylene tetraamine, poly(oxypropylenediamine), and poly(oxypropylenetriamine).

Other suitable curing agents for epoxy resins include the cycloaliphatic amines such as isophorone diamine, 1,2-diaminocyclohexane, and N-aminoethylpiperazine. Also, aromatic amines can be used, including 4,4'-diamino-diphenyl methane, 4,4'-diaminodiphenyl sulfone, and m-phenylene diamine.

Still other curing agents for epoxy resins which can be used in the resin systems of the invention include polyamidoamines, polyamides, anhydrides, dicyandiamides, polycarboxylic polyesters, isocyanates, phenylformaldehyde novolacs, polysulfides and polymercaptans, melamine-formaldehyde, ureaformaldehyde, and resole phenolics.

The polymerization reaction for the resin systems is initiated by adding the curing agent to the system. The rate of reaction will increase with an increase in temperature. The specific temperature used will depend on processing factors related to the end use of the resin systems.

The rate of cure of the resins depends on many factors, including the nature of the resin itself, copolymers, additives, and strength and amount of curing agent or hardener employed. In general, however, in the case of preferred epoxy resins which are diglycidyl ethers of bisphenol A, such resins are cured at temperatures ranging from about 80° to about 200° C., for periods of time ranging from about 1 to about 5 hours. Epoxies of greater strength are obtained when higher curing temperatures are used.

Simultaneously with the polymerization of the resin, the amount of fluorescence from the resin system is measured. The measurement can be made with a fiber optic probe inserted into the reaction mixture which is coupled to appropriate devices for measuring the fluorescence emissions. The basic components of a preferred fiber optic fluorometer comprise a light source consisting of an incandescent lamp; an excitation filter which provides a specific spectral region; condensing lenses; an optical wave guide consisting of a silica-clad, all-silica fiber core; a beam splitter; an emission filter, and a photodetector.

Alternatively, a sample of the resin is obtained and placed in a conventional fluorometer for analysis of emissions.

The examples below illustrate the practice of the method of the invention, but are not to be construed as limiting the scope thereof in any manner.

EXAMPLE 1

An epoxy resin system is prepared by mixing a stock solution of about 117 ppm by weight fluorescein in diamino cyclohexane, with TACTIX 123 ® epoxy resin, a diglycidal ether of bisphenol A. The diamino cyclohexane comprises about 17 percent by weight of the total mixture. A thick (about 2 to 4 mm) film of this resin system is prepared by pouring the mixture into a clean aluminum pan. The film is heated to a temperature of about 90° C. for about 28 minutes. The film is cooled and the emission spectra of the film is measured at room temperature. The film is again heated for about 20 minutes and the spectra is again recorded. This is repeated at about 20 minute intervals until about 88 minutes of total heating at about 90° C. is reached.

The excitation is about 520 nm and the data is collected on a Fluorolog 2 fluorimeter operating in the "front face" mode. In this mode, the emission beam is 20 degrees off the excitation beam. The spectral data collected is shown in FIG. 4, where the individual spectra represents data collected at intervals of about 28, 48, 68, and 88 minutes over the period of about 88 minutes. Spectra 1 is the spectra obtained after about 28 minutes of heating, Spectra 2 is the spectra obtained after about 48 minutes of heating, Spectra 3 is the spectra obtained after about 68 minutes of heating, and Spectra 4 is the spectra obtained after about 88 minutes of heating.

EXAMPLE 2

An epoxy resin system is prepared comprising a mixture of TACTIX 123 ® epoxy with about 17 percent by weight diamino cyclohexane solution containing about 117 ppm fluorescein. About a 2–4 mm thick film is prepared by pouring the mixture into an aluminum pan. The film is heated for about 20 minutes at about 80° C., then further cured at about 120° C. for about one hour. Excitation spectra were taken at two different stages of cure at a fixed emission of about 675 nm. The results are shown in FIG. 5, in which Spectra 1 is the value obtained after the film had been heated for about 20 minutes at about 80° C., and Spectra 2 is the value obtained after further cure at about 120° C. for about one hour.

EXAMPLE 3

An epoxy resin system is prepared by mixing TACTIX 123 ® epoxy resin and about 17 percent by weight of a diamino cyclohexane containing about 117 ppm dibromo fluorescein diacetate. A film is prepared by pouring the mixture into a clean aluminum pan. The film is heated to about 80° C. for about 20 minutes, then reheated to about 120° C. for about one hour. Excitation and emission spectra are obtained, and are shown in FIG. 6. In FIG. 6, Spectra 1 is an emission spectra done with a fixed excitation at about 520 nm, and scanned from about 540 to 700 nm with one heat treatment. Spectra 2 is an emission spectra with the excitation at about 520 nm and the emission scanned from about 540 to 700 nm done after the second heat treatment Spectra 3 is an emission spectra done with a fixed emission at about 444 nm and scanned from about 470 to 700 nm done after one heating cycle. Spectra 4 is an emission spectra with the excitation at about 444 nm and the emission scanned from about 470 to 700 nm done with both heating cycles.

EXAMPLE 4

An epoxy resin system is prepared by mixing D.E.R. 332 ® epoxy resin, a diglycidal ether of bisphenol A, available from The Dow Chemical Company, with about a 17 percent by weight solution of PAC 1482 ®, a mixture of methylene dianiline and phenylene diamine, available from Pacific Anchor Company, containing about 117 ppm acridine yellow. The total dye concentration is about 20 ppm by weight based on the resin system.

The mixture is initially heated to a temperature of about 90° C. for about 1½ hours and brought to the glassy stage, then it is further heated to a temperature of about 120° C. for about 1½ hours to effect complete cure.

Emission spectra are obtained at three stages. The data is shown in FIG. 7. Spectra 1 is the emission spectra of the mixture taken prior to heating, Spectra 2 is the emission spectra taken when the mixture is at the glassy stage, and Spectra 3 is the emission spectra taken at cure.

EXAMPLE 5

In this example, a series of epoxy resin systems are studied which contain various dyes. The epoxy resin systems are prepared generally in accordance with the procedures set forth in Examples 1–4 above.

Some systems contain an epoxy resin and dye dissolved in a solvent, without a curing agent being present, while others contain an epoxy resin, curing agent, and dye.

Measurements are made of emission wavelengths, and the ratios of two emission wavelengths are calculated at two different degrees of reaction and divided by each other.

The significance of this procedure is that it allows one to compare the relative amounts of different chemical species present at various stages, thereby enabling the extent of cure to be determined.

Another ratio measures the intensity of a single wavelength at two different stages of cure.

The resin systems, excitation wavelength, treatment schedule, and ratios of emissions are set forth in Table I below. All spectral measurements are taken on a Fluorolog 2 fluorimeter.

TABLE I

| Composition Dye | Epoxy Resin | Curing Agent | Solvent | Excitation Wavelength (nm) | Treatment Schedule | Ratio 1 | Ratio 2 | Ratio 3 |
| --- | --- | --- | --- | --- | --- | --- | --- | --- |
| 1. Fluorescein diacetate | DER 332① | PAC 1482③ | | 430 | 1½ hrs @ 90° C. vs. 1½ hrs @ 90° C. + 1½ hrs @ 130° C. | 550/500 1.488888 | 600/500 1.46666 | 550 1.240740 |
| 2. Fluorescein diacetate | DER 332① | | xylene | 460 | | 550/500 2.782548 | 600/500 3.918282 | 550 0.804914 |
| 3. 2,7-dichlorofluorescein | TACTIX 123② | H31④ | | 520 | 20 min @ 80° C. vs. 20 min @ 80° C. + 1 hr @ 120° C. | 620/585 0.607476 | 650/585 0.444444 | 620 0.607476 |
| 4. diiodofluorescein | TACTIX 123② | H31④ | | 520 | 20 min @ 80° C. vs. 20 min @ 80° C. + 1 hr @ 120° C. | 590/550 0.557651 | 660/550 0.260807 | 590 0.351851 |
| 5. Eosin Y Lactone | TACTIX 123② | | xylene | 530 | | 590/550 0.940404 | 660/550 0.890909 | 600 0.872972 |
| 6. Eosin B | TACTIX 123② | | xylene | 530 | | 590/550 1.255462 | 660/550 1.4 | |
| 7. Rose Bengal | DER 332① | PAC③ 1482 | | 510 | 1 hr @ 90° C. vs. 1 hr @ 90° C. + 1½ hrs @ 130° C. | 590/550 1.056105 | 660/550 1.019810 | 600 0.891089 |
| 8. Acridine Yellow | TACTIX 123② | | xylene | 435 | | 525/550 1.166387 | 600/500 1.067307 | 525 5.003236 |
| 9. 2-aminoanthrascene | TACTIX 123② | H31④ | | 480 | 18 min @ 90° C. vs. 18 min @ 90° C. + ½ hr @ 120° C. | 550/525 1.047619 | 600/525 1.028571 | 550 1.527777 |

TABLE I-continued

| Composition Dye | Epoxy Resin | Curing Agent | Solvent | Excitation Wavelength (nm) | Treatment Schedule | Ratio 1 | Ratio 2 | Ratio 3 |
|---|---|---|---|---|---|---|---|---|
| 10. 3-amino-fluoroanthene | DER 332① | PAC 1482③ | | 510 | 18 min @ 92° C. vs. 18 min @ 92° C. + ½ hr @ 120° C. | 560/540 1.111300 | 600/540 1.259202 | 560 1.810344 |

①DER 332 ® epoxy resin is a diglycidal ether of bisphenol A
②TACTIX 123 ® epoxy resin is a diglycidal ether of bisphenol A
③PAC 1482 ® curing agent is a mixture of methylene dianiline and phenylene diamine
④H31 ® epoxy resin hardener is a diamino cyclohexane In compositions 2, 5, 6, and 8 set forth in Table I, the dyes are first dissolved in N-methyl-2-pyrrolidinone and then into the epoxy resin. The solutions are then either heated to about 120° C. for about two hours or left at room temperature. Small portions of the resulting solution are then dissolved in xylene and the fluorescent spectra taken in accordance with the treatment schedule. These results indicate such dyes do react with the epoxy resin. This procedure eliminates the interaction with the amine curing agent which simplifies the analysis.

Ratio 3 is obtained in the following manner, composition 1 in Table I, being used as an example.

$$\text{Ratio 3} = \frac{\left(\frac{\text{F550 at 90° C. for 1½ hours}}{\text{F500 at 90°C. for 1½ hours}}\right)}{\left(\frac{\text{F550 at 90° C. for 1½ hours} + 130° \text{C. for 1½ hours}}{\text{F500 at 90° C. for 1½ hours} + 130° \text{C. for 1½ hours}}\right)}$$

EXAMPLE 6

An epoxy resin system is prepared by mixing a diglycidal ether of bisphenol A (D.E.R. 332 ® epoxy resin), with a curing agent comprising a mixture of methylaniline dianiline and phenylene diamine (PAC 1482 ® curing agent), and fluorescein. The mixture is cured by heating and spectral data is obtained during the cure. The emission spectra at two wavelengths are divided by each other to give a fluorscence ratio and plotted vs. the extent of reaction (FIG. 2). The extent of reaction is determined by measuring the residual exotherm obtained by differential scanning calorimetry from the epoxy, diamino cyclohexane, and fluorescein mixture that exhibits the same thermal history as the epoxy films described in Examples 1-5. The graph shown in FIG. 2 illustrates that large changes in the fluorescent ratios occur during the latter part of cure, thus demonstrating the high sensitivity of this method with respect to measuring the latter stages of cure.

EXAMPLE 7

An epoxy resin system is prepared by adding fluorescein to a mixture of TACTIX 123 ® epoxy resin and H31 ® epoxy resin hardener, available from The Dow Chemical Company. The resin system is cured by heating. Spectral data is gathered during the cure. The emission spectra at two wavelengths are divided by each other to give a fluorscence ratio and plotted vs. the extent of reaction. See FIG. 3. The extent of reaction is determined by measuring the residual exotherm from epoxy, diamino cyclohexane, fluorescein mixtures that possess the same thermal history as the epoxy films of Examples 1-5.

EXAMPLE 8

An epoxy resin system is prepared comprising about 20 ppm fluorescein, TACTIX 123 ® epoxy resin, and about 17 percent by weight H31 ® epoxy resin hardener. This resin system serves as the resin matrix in the formation of a carbon fiber composite, in which the resin system comprises about 50 percent by weight of the composite. The composite is cured at about 80° C. During cure, emission spectra are taken using a 700 micron diameter glass core, glass clad, polyimide coated optical fiber embedded in the carbon fiber composite. The excitation is at about 520 nm. Emission spectra are recorded on a graph, FIG. 1, as a fluorescence ratio as a function of time. The fluorescence ratio is calculated as the emission at about 550 nm divided by X, the emission at various points. Time 0 on the graph represents the glassy stage of the resin system. Values are recorded at various intervals for about 80 minutes thereafter. The change in slope over time demonstrates the sensitivity of the method of the invention in determining extent of cure in the final stages.

In carrying out the process of this invention, the analysis of the fluorescence to be performed depends upon the application. For example, the amount of light emitted at a specific wavelength or group of wavelengths may be followed. Taking the ratio of two wavelengths allows one to compare the relative amounts of different chemical species. More complicated multiple wavelengths analysis enables one to identify many chemical species. Changing the excitation wavelength or wavelengths gives different sensitivities for different chemical species.

Important data to be observed from the tables above, and the figures to which references are made, is the comparison of the extent of reaction obtained from DSC (Differential Scanning Calorimetry) of the curing epoxy verses the ratio of the fluorescence emission of two or more wavelengths with a fixed excitation. The data from the graphs shows a very high sensitivity for especially about the last 10 percent of reaction.

For further details of the DSC test method, see duPont 1090 *Thermal Analyzer Operators Manual*, duPont, Analytical Instruments Division, Concord Plaza-McKean Building, Wilmington Del. 19898, May 1982, the relevant portions incorporated herein by reference for all legal purposes served thereby.

EXAMPLE 9

Another series of experiments is undertaken, duplicating in part the tests set forth in Example 5, wherein different dyes are evaluated by calculating the ratios of the intensity of the fluorescent emissions at various stages of cure of the resin system. The system is a mixture of TACTIX 123 ® epoxy resin and H31 ® epoxy resin hardener. The dyes are dissolved in N-methyl-2-pyrrolidinone to facilitate dissolution. Then dyes are diluted with methanol before measuring their absorption in the 400 to 700 nm range. Several of the dyes do not absorb in this range until the solution pH is adjusted to 11. The dyes are dissolved in H31 ® epoxy resin hardener such that the absorbance at the absorbance maximum is in the visible range in the final amine epoxy mixture.

The data is set forth in Table II below.

TABLE II

| Dye | Excitation Wave-length (nm) | Ratio C | Excitation Wave-length (nm) | Ratio D |
| --- | --- | --- | --- | --- |
| 2,7 dichlorofluorescein | 520 | 1.009 | 530 | 1.72 |
|  | 530 | 0.9974 |  |  |
| Erythrosin B | 520 | 1.045 | 530 | 1.52 |
|  | 530 | 1.025 |  |  |
| Rhodamine B | 520 | 1.67 | 530 | 0.52 |
|  | 530 | 1.88 |  |  |
| Eoxin Y | 520 | 0.9215 | 530 | 1.52 |
|  | 530 | 0.843 |  |  |
| Tetrachlorofluorescein | 520 | 1.05 | 530 | 1.54 |
| Eosin B | 520 | 1.19 | 530 | 1.25 |
|  | 530 | 1.16 |  |  |
| Diidofluorescein | 520 | 0.9689 | 530 | 1.59 |
|  | 530 | 1.0549 |  |  |
| Fluorescein | 520 | 0.8171 | 520 | 0.44 |
| Dichlorofluoroescein diacetate | 520 | 1.035 | 520 | 1.152 |
|  | 530 | 1.021 |  |  |
| Fluorescein diacetate | 520 | 1.13 | 520 | 4.95 |
|  | 530 | 1.14 |  |  |
| Fluoroescein Hg Acetate | 520 | 1.475 | 520 | 2.88 |
|  | 530 | 1.393 |  |  |

In Table II is data representing the evaluation of different fluorescein derivatives in epoxy resin systems. The ratio of the intensity of emissions at 600 nm and 550 nm with one or more excitation wavelengths is calculated. This is done at different stages of cure. The ratios of these two numbers indicate how much the spectra changes between the two stages of cure. These cures are done at about 80° C. to provide sufficient time to compare the different stages of cure. The calculations are as follows:

$$\frac{\text{Intensity at 600 nm for 20 min. of cure}}{\text{Intensity at 550 nm for 20 min. of cure}}.$$

The value obtained is then divided by the same ratio at about 85 min. into the cure to give a final ratio, designated Ratio C.

Another ratio of intensities compared the change in total fluorescent intensity at 550 nm (intensity at about 20 min. of cure/intensity at about 85 min. of cure). This is designated Ratio D.

EXAMPLE 10

A resin system comprising TACTIX 123 ® epoxy resin and H31 ® curing agent with about 50 ppm of 3-amino fluoranthene is prepared in a manner similar to that previously described. The emission spectra at two different excitation wavelengths (510 nm and 520 nm) after curing about 18 minutes at about 92° C. and after curing about an additional 30 minutes at about 120° C. are compared in FIG. 9. Spectra 1 is 510 nm at 92° C. for 18 min., Spectra 2 is 520 nm at 92° C. for 18 min., Spectra 3 is 510 nm at 120° C. for an additional 30 min., and Spectra 4 is 520 nm at 120° C. for an additional 30 min.

EXAMPLE 11

A urethane resin system is prepared using a prepolymer formed from HMDI (hydrogenated methylene diphenyl diisocyanate) and castor oil. The hardener used by weight is about 75 percent castor oil and about 25 percent pentaerythritol. The final isocyanate to hydroxyl (from castor oil) ratio is close to 1, except for the added glycerol in sample 3 below.

Three samples are prepared. All are a 1 to 1 weight ratio (molar ratio hydroxyl from castor oil to isocyanate). Sample 1 contains no fluorescein, sample 2 is prepared using a fluorescein saturated hardener, and sample 3 is prepared the same as sample 2 except 1 ml. of glycerol is added to the 1 ml. of hardener added to 107 ml. of prepolymer. The fluorescein saturated hardeners for samples 2 and 3 are obtained by adding fluorescein to the hardener, then heating at about 80° C. for about 24 hours, and setting at room temperature for three days.

Thick films (2–4 mm) of each sample are prepared on clean aluminum pans and heated for about 24 hours at about 80° C.

Spectra of each sample are taken at an excitation of 460 nm.

The spectra are shown in FIG. 8. Spectra 1 is obtained from sample 1, Spectra 2 from sample 2, and Spectra 3 from sample 3.

The spectra shown in FIG. 8 demonstrate that the extent of reaction of isocyanates with free hydroxyls or phenolics can be measured by the process of the invention.

EXAMPLE 12

An epoxy resin system is prepared by mixing a quantity of TACTIX 123 ® epoxy resin with about a 17 percent by weight H31 ® epoxy resin hardener containing about 20 ppm Rhodamine 123. The system is heated at about 80° C. until it reaches the glassy cure stage. Spectra are taken at various stages of cure. In the early stages of cure, the system is very fluorescent, but it becomes non-fluorescent by the time it reaches the glass stage. This demonstrates that the process described herein can be used to monitor the earliest part of the cure as well as the latter stages, by selection of appropriate dyes.

The values obtained from the foregoing examples demonstrate the high sensitivity found when using fluorescein as a probe of cure. These dyes are superior because the excitation is in the visible range and the dye fluorescence is minimally overlapped with the inherent fluorescence found in these epoxy hardener systems. Further advantages of working in the visible spectrum, include the fact that transmission through fiber optics is high, and the sensors and light sources are inexpensive.

Preferably, the excitation wavelength of light used to elicit fluorescent emissions from the dye-resin systems of this invention ranges from about 350 nm to about 700 nm, preferably from about 400 nm to about 600 nm, and most preferably from about 450 nm to about 550 nm.

Although the process of the invention is most advantageously used in connection with the visable light spectrum, it is also appreciated that it can be used with ultraviolet light if desired. Therefore, the process of this invention is intended to cover the use of all types of light, whether visable or ultraviolet, to elicit fluorescent emissions from the dyes described herein.

If desired, more than one dye can be used in the method of the invention. This is advantageous when different dyes react and bond to the resin at different reaction sites and at different stages in the curing cycle. This enables more accurate analysis of the rate and extent of cure of the resin system to be made. For example, a first dye can be used which exhibits maximum fluorescence during the first part of the reaction, and a second dye can be used which exhibits maximum fluorescence during the latter stages of the reaction. By proper calibration, total monitor of the cure can be realized.

The method of the invention can also be used to track extent and rate of cure in resin systems when the resin is incorporated into a composite material. This is exhibited in FIG. 1, which shows a fiber optic determination of cure in a fluorescein, carbon fiber composite.

The present invention may be embodied in other specific forms without departing from the spirit and scope thereof. These and other modifications of the will occur to those skilled in the art and are intended to fall within the scope of the appended claims.

What is claimed is:

1. A method for measuring the rate and extent of cure of a resin system undergoing polymerization which comprises:
    A. adding at least one multifunctional fluorescent dye, in an amount sufficient to produce a measurable change in fluorescence, to the resin system comprising a resin undergoing polymerization, said dye being one which initially complexes with itself or with other components of the system, and subsequently chemically reacts with the resin and which degree of fluorescence of said dye varies in accordance with the degree of reaction with the resin;
    B. polymerizing said resin to cure said resin system;
    C. simultaneously measuring the fluorescence of the resin system using a probe and monitoring system; and
    D. comparing the measured fluorescence at one or more wavelengths with pre-existing baseline values which are correlated with the extent of cure, whereby the rate and extent of cure of the system being evaluated is determined, wherein said multifunctional fluorescent dye is selected from the group consisting of (a) fluorescein, fluorescein diacetate, halo-substituted fluorescein, and nitro-substituted fluorescein, and (b) acridine, amino-substituted acridine, and lower alkyl-substituted acridine.

2. The method of claim 1 wherein said dye is selected from the group consisting of fluorescein, dibromodinitrofluorescein, tetraiodotetrachlorofluorescein, tetrabromofluorescein, 4',5'-dibromofluorescein, 2',7'-dichlorofluorescein, and 4',5-diiodofluorescein.

3. The method of claim 1 wherein said dye is selected from the group consisting of acridine, amino-substituted acridine, and lower alkyl substituted acridine.

4. The method of claim 1 wherein said resin is an epoxy resin.

5. The method of claim 1 wherein said resin is a urethane resin.

6. The method of claim 1 wherein said measurement of fluorescence of said resin system is accomplished using a fiber optic probe inserted into said system.

7. The method of claim 1 wherein said measurement of fluorescence of said resin system is accomplished using a fluorometer.

8. The method of claim 1 wherein said resin system is heated to a temperature of from about 80° to about 200° C. while undergoing polymerization.

9. The method of claim 1 wherein the rate and extent of cure in the last 10 percent of the cure reaction is determined from said fluorescence measurements of the reaction system during polymerization.

10. The method of claim 1 wherein the amount of dye in said resin system is between about 1 to about 100,000 parts per million by weight.

11. The method of claim 1 wherein said resin is selected from the group consisting of polyethylene and copolymers, vinyls, polystyrene and copolymers, phenolics, polypropylene and copolymers, ureas and melamines, alkyds, polyesters, polyurethanes, polyacetals, polycarbonates, styrene-butadiene elastomers, acrylonitrile-butadiene elastomers, and acrylics.

12. The method of claim 3 wherein said dye is acridine yellow.

13. The method of claim 4 wherein said epoxy resin is a diglycidal ether of bisphenol A.

14. The method of claim 6 wherein said measurement of fluorescence of said resin system is accomplished using the fiber optic probe using a light wavelength of from about 400 nm to about 600 nm.

15. A method of measuring the rate and extent of cure of a resin system undergoing polymerization wherein the resin system comprises a thermosetting plastic resin and a curing agent therefore which comprises:
    A. adding at least one multifunctional fluorescent dye in an amount sufficient to produce a measurable change in fluorescence, to the curing agent, said dye being one which initially complexes with itself or with other components of the system and subsequently chemically reacts with the resin and which degree of fluorescence varies in accordance with the degree of reaction with the resin;
    B. mixing said curing agent with said thermosetting plastic resin;
    C. polymerizing said thermosetting plastic resin to cure said resin system; and
    D. simultaneously measuring the fluorescent emissions of said resin system;
    E. comparing the measured fluorescent emissions at one or more wavelengths with pre-existing values which are correlated with the extent of cure, whereby the rate and extent of cure of the system being evaluated is determined;

wherein said multifunctional fluorescent dye is selected from the group consisting of (a) fluorescein, fluorescein diacetate, halo-substituted fluorescein, and nitro-substituted fluorescein, and (b) acridine, amino-substituted acridine, and lower alkyl-substituted acridine.

16. The method of claim 15 wherein said thermosetting plastic resin is an epoxy resin.

17. The method of claim 15 wherein said thermosetting plastic resin is a polyurethane.

18. The method of claim 16 wherein the amount of dye in said resin system is between about 10 to about 30 parts per million by weight.

* * * * *